United States Patent [19]
Palfray

[11] Patent Number: 5,116,381
[45] Date of Patent: May 26, 1992

[54] PROSTHESIS WITH A MONOBLOC FRAMEWORK FOR LEG AMPUTATION AND METHOD FOR PRODUCING THIS PROSTHESIS

[75] Inventor: Michel Palfray, Seurre, France

[73] Assignee: Etablissements Proteor, France

[21] Appl. No.: 690,051

[22] Filed: Apr. 23, 1991

[30] Foreign Application Priority Data

Apr. 23, 1990 [FR] France ................... 90 05126

[51] Int. Cl.$^5$ .................... A61F 2/60; A61F 2/66
[52] U.S. Cl. ...................... 623/33; 623/550; 623/55; 623/901
[58] Field of Search ............ 623/27, 33, 38, 53, 623/55, 47, 50, 901, 35

[56] References Cited

U.S. PATENT DOCUMENTS

| 470,431 | 3/1892 | Marks | 623/33 |
| 2,379,538 | 7/1945 | Meierhofer | |
| 3,909,855 | 10/1975 | Barreob | |
| 4,911,724 | 3/1990 | Fikes | 623/37 |
| 4,959,073 | 9/1990 | Merlette | 623/55 |
| 5,004,477 | 4/1991 | Palfray | 623/53 |

FOREIGN PATENT DOCUMENTS

| 0405686 | 11/1924 | Fed. Rep. of Germany | 623/53 |
| 690657 | 9/1930 | France | |
| 1162321 | 9/1958 | France | |
| 0806026 | 2/1981 | U.S.S.R. | 623/27 |
| 2202448 | 9/1988 | United Kingdom | |

*Primary Examiner*—Randall L. Green
*Assistant Examiner*—D. Willse
*Attorney, Agent, or Firm*—Scully, Scott, Murphy & Presser

[57] ABSTRACT

The invention relates to a prosthesis for a leg amputee, comprising a thermoformed framework made of a thermoplastic material or of a laminated substance, covered with a coating material and comprising a socket (1), a leg part (2) and a prosthetic foot (3), one adjoining the other.

According to the invention, the framework of the leg part (2) and the prosthetic foot (3) constitutes a monobloc assembly, produced in a single casting operation, and in that the prosthetic foot comprises, at the level of the sole, a cut having served for the extraction of the molding core and, at the level of the heel, above the sole, a cut (9) of wedge formation lending itself to a flexion of the rear of the sole relative to the leg part.

16 Claims, 4 Drawing Sheets

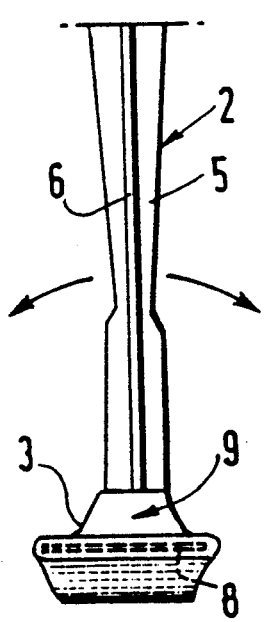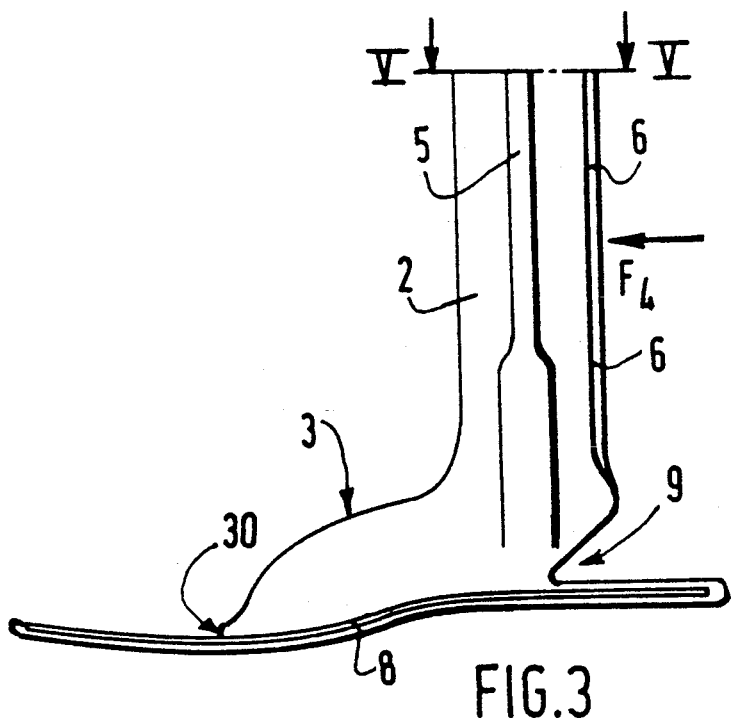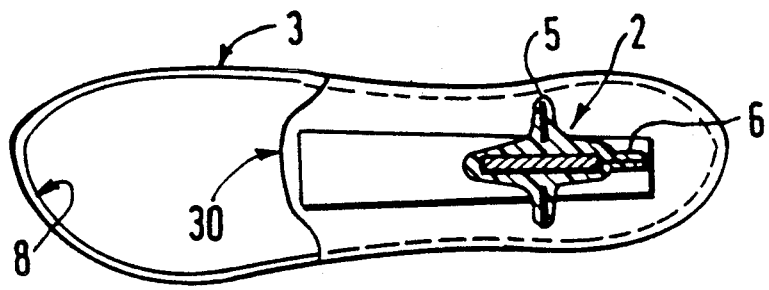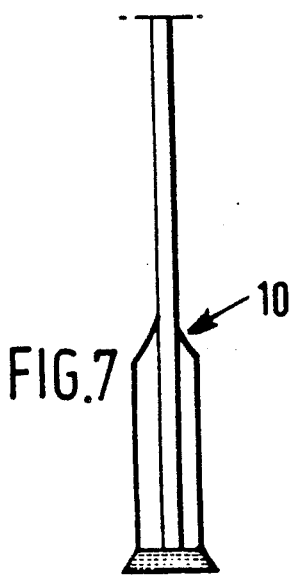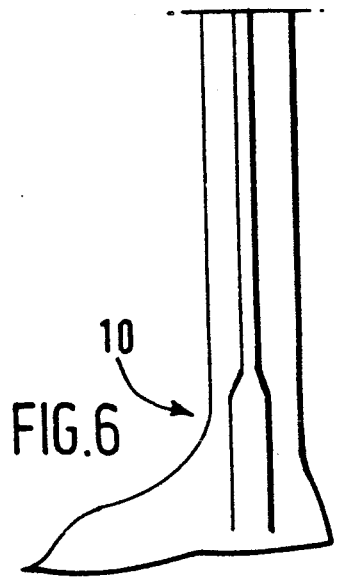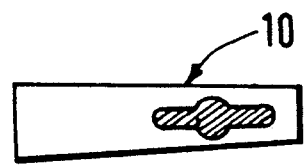

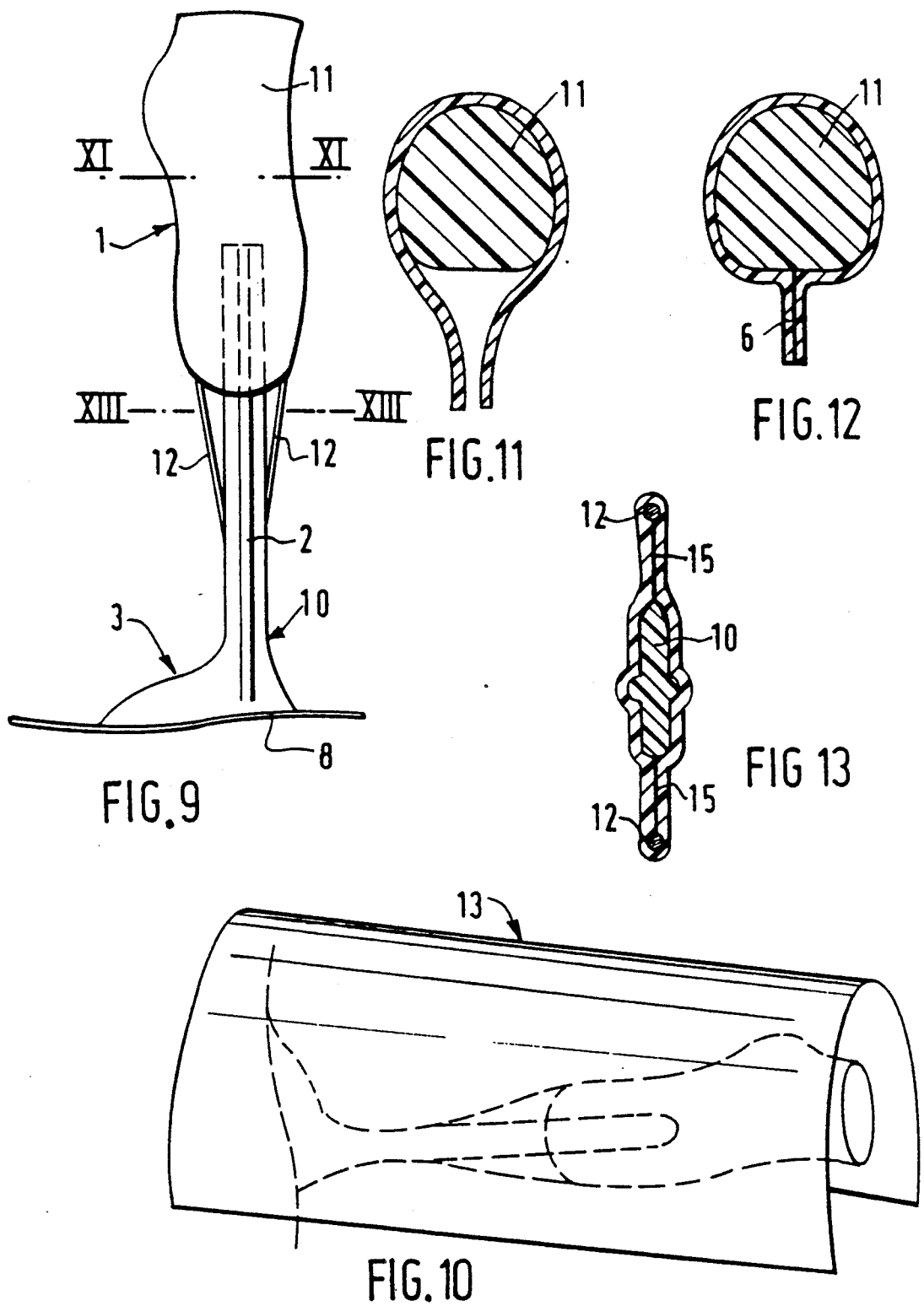

PROSTHESIS WITH A MONOBLOC FRAMEWORK FOR LEG AMPUTATION AND METHOD FOR PRODUCING THIS PROSTHESIS

The present invention relates to a prosthesis with a monobloc framework for leg amputation. The invention also relates to a method for producing such a prosthesis.

The usual prostheses for leg amputation generally comprise three main elements:

a part forming a sheath, a so-called socket, in which the stump of the amputee engages and which can be made integral with this stump;

a prosthetic foot;

and a leg part joining the socket and the prosthetic foot.

These elements are produced separately and are then assembled so as to form the prosthesis. They can be made of different materials, but the resulting prosthesis is generally heavy, in particular because of the structure of the prosthetic foot, and the latter often has a poor mechanical strength.

For this reason, these prostheses are unsuitable for elderly persons who, on the one hand, move about very little and do not therefore need a complex prosthesis and who, on the other hand, tire very quickly if the prosthesis is too heavy.

The present invention aims to overcome these disadvantages by proposing a prosthesis for leg amputation which is much lighter and of a simpler structure than those of the conventional techniques, and which is therefore particularly well suited to use in elderly subjects.

The invention also aims to propose a prosthesis of this type which can be produced in monobloc form by a method which is easy to implement.

Another aim of the invention is to propose a prosthesis of the abovementioned type, in which the prosthetic foot affords great flexibility upon walking, by giving it an energy-recovering effect.

Finally, the invention aims to propose such a prosthesis which is of a reduced manufacturing cost.

To this end, the invention relates to a prosthesis for a leg amputee, comprising a thermoformed framework made of a thermoplastic material or of a laminated substance, covered with a coating material and comprising a socket, a leg part and a prosthetic foot, one adjoining the other, characterized in that the framework of the leg part and of the prosthetic foot constitutes a monobloc assembly, produced in a single casting operation, and in that the prosthetic foot comprises, at the level of the sole, a cut having served for the extraction of the molding core and, at the level of the heel, above the sole, a cut of wedge formation lending itself to a flexion of the rear of the sole relative to the leg part.

Preferably, the socket will also be cast in one piece with the leg part and the prosthetic foot, but it will also be possible for it to be added to the latter and comprise, for example, a projecting part of U-shaped cross-section at its lower part, capable of fitting over a projecting part of complementary profile formed at the upper part of the leg part and intended to be fixed on the latter in the most appropriate position with the aid of screws and nuts.

The invention also relates to a method for producing such a prosthesis, characterized in that a monobloc framework of the leg part and of the prosthetic foot is cast in a thermoplastic material or a laminated substance around a suitable core, and in that, after casting, the sole of the prosthetic foot is cut in order to extract the core, and in that there is formed in the cast framework, at the level of the heel of the prosthetic foot and above the sole, a cut of wedge formation lending itself to a flexion of the rear of the sole relative to the leg part.

Advantageously, a reinforcement sole of a material capable of deforming elastically, for example of carbon and glass composite or any other material capable of elastic deformation, will be incorporated in the prosthetic foot. It will be possible for this sole to be fixed below the core used for the molding, prior to the production of the monobloc framework of the prosthesis.

For the purpose of increasing the effects of energy recovery in the prosthesis during walking, it will also be possible for a metallic spring blade to be incorporated in the prosthetic foot above the sole made of an elastically deformable material, it being curved between the front part and the rear part of the sole.

When the socket is to be produced at the same time as the leg part and the prosthetic foot, likewise by casting, a plaster model reproducing the shape of the stump will be fixed in the corresponding position on the core used for the casting.

Advantageously, ribs will be made at the front and at the rear of the leg part, these ribs being made easily, as will be described hereinbelow, by stretching a metal wire obliquely between the base of the socket and the leg part, to the front and to the rear of the latter.

Other characteristics and advantages of the invention will emerge from the following detailed description of various embodiments, given by way of non-limiting example. In this description, reference will be made to the attached diagrammatic drawings in which:

FIG. 3 is a view, on an enlarged scale, of the lower part of FIG. 1;

FIG. 4 is a view following the arrow $F_4$ in FIG. 3;

FIG. 5 is a cross-section, with partial cut-away, along the line V—V in FIG. 3;

FIGS. 6, 7 and 8 are side-elevation, front and plan views, respectively, of the metal core used to carry out the casting of the prosthesis framework according to the invention;

FIG. 9 is a view analogous to FIG. 8 (sic), in the case of the production of a prosthesis framework with the socket adjoining;

FIG. 10 illustrates an example of vacuum thermoforming applied to the core in FIG. 9;

FIGS. 11 and 12 are cross-sections on an enlarged scale, illustrating two phases of the thermoforming of the framework at the level of line XI—XI in FIG. 9;

FIG. 13 is a cross-section illustrating the thermoforming at the level of the line XIII—XIII in FIG. 9;

Figure 2:
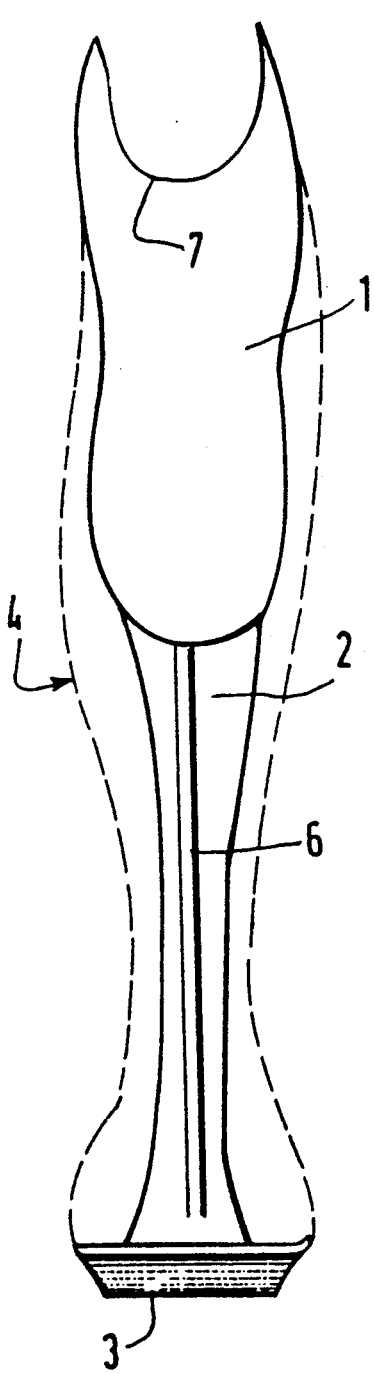
FIGS. 1 and 2 are views, in side elevation and from the rear respectively, of a monobloc prosthesis framework according to the invention, with the profile of the prosthesis shown by broken lines.
Figure 1:
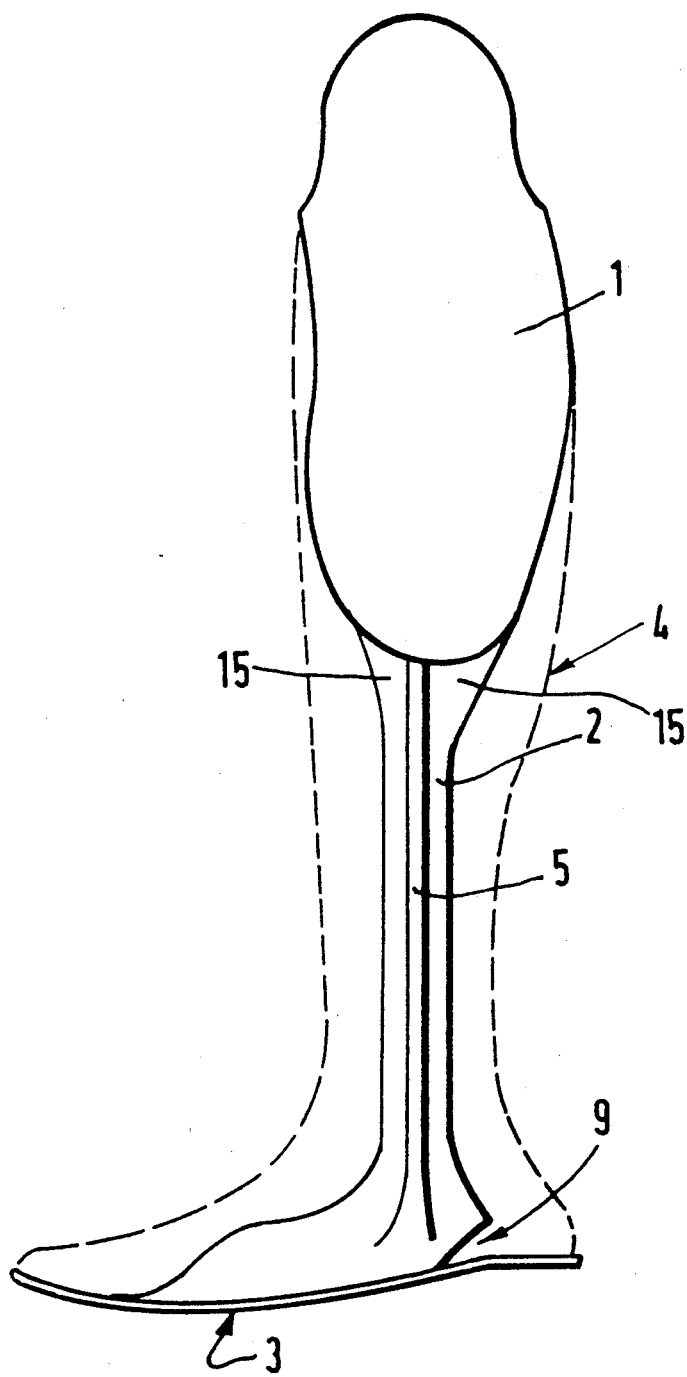

Reference will be made first to FIGS. 1 to 5 which show a monobloc prosthesis framework according to the invention, with a socket 1, intended to receive the stump of the amputee, a leg part 2 adjoining the socket 1 and made in one piece with the latter by thermoforming, and a prosthetic foot 3 adjoining the leg part 2 and made in one piece with the latter by thermoforming. This framework is intended to receive subsequently a lining 4, for example of a flexible foamy plastic, imitating the shape of the limb.

The leg part 2 has two lateral ribs 5 and, at the rear, a rib 6 formed by welding of the material used for the thermoforming of the framework, a polyolefin, for example. The socket 1 has been cut into at 7 in the usual manner after thermoforming.

As will be seen more clearly in FIGS. 3, 4 and 5, the prosthetic foot 3 comprises a reinforcement sole 8 made of carbon composite or any other elastic material, which is covered, at the front and at the rear, with the thermoforming material and whose aim is to give to the prosthetic foot a spring action when the amputee is walking. Various soles 8 can be used, depending on the weight and the activity of the amputee, in order to modulate the desired spring action. In order to confer flexibility upon the thermoformed sole of the prosthetic foot and upon the sole 8, the front upper part of the prosthetic foot will advantageously be cut at 30, as well as, if appropriate, the part of the sole of the prosthetic foot arranged below this cut 30. For the same purpose, a cut 9 of wedge formation is made at the level of the prosthetic heel, between the sole and the leg part, in order to confer flexibility upon the prosthesis which, at each step taken by the amputee, returns elastically to its initial position.

The metal core 10, used to produce the prosthesis according to the invention by casting or by thermoforming, is shown in FIGS. 6, 7 and 8.

Before proceeding to the casting, the reinforcement sole 8 is fixed under the base part of the core 10. If it is desired to produce the socket 1 at the same time, the head of the core 10 is embedded in a plaster reproduction 11 of the amputee's stump 1. In order to strengthen with ribs 15, directed towards the front and towards the rear, the part of the framework of the prosthesis connecting the leg part to the socket, two metal wires 12 will be stretched obliquely between the base of the plaster cast 11 of the stump and the core 10 (FIG. 9).

The vacuum thermoforming of the prosthesis framework will then be carried out, for example in the usual manner, by enveloping in a sheet of polyethylene 13 or of another thermoplastic material the core 10 thus equipped (FIG. 10), by heating the sheet 13 in such a way that it softens (FIG. 11) and by subjecting it to partial vacuum so that it bears tightly against the core 10, the sole 8, the cast 11 and the metal wires 12 (FIGS. 12 and 13), thus giving rise to the weld 6, which forms a rear rib (FIG. 12), and to two lateral reinforcement ribs 15 (FIG. 13).

After thermoforming of the prosthesis, the sole 8 of carbon composite and its sheath of polyethylene are cut at the base of the core 10 in order to permit the extraction of the latter and the plaster cast 11 is destroyed in order to disengage the socket 1, which is then cut to the desired shape.

It will be noted that the leg part 2 can have a cross-section of absolutely any shape.

As has been indicated hereinabove, the prosthetic foot 3 of the prosthesis framework can be equipped with a metallic spring blade in order to obtain an increased energy recovery effect while the amputee is walking.

Figure 14:
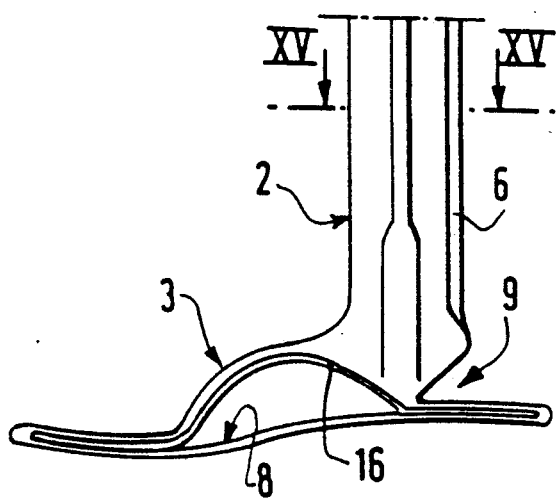
FIGS. 14 and 15 are views, analogous to FIGS. 3 and 5 respectively, of a variant of the prosthesis framework according to the invention in which a curved spring blade is inserted in the prosthetic foot.
Figure 15:
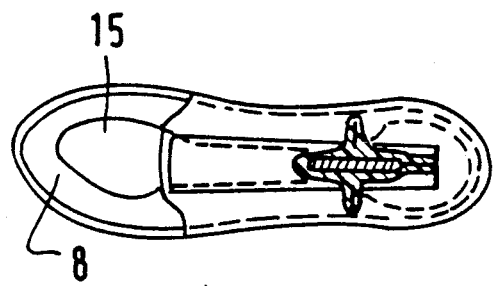

This is what is shown in FIGS. 14 and 15, which are to be compared with FIGS. 3 and 5. It will be seen that a spring blade 16 has been introduced into the foot through the opening made for the extraction of the thermoforming core, and that the blade 16 is curve between the front and rear ends of the prosthetic foot, against which ends it is braced, thereby giving this foot an increased flexibility.

Figures 16, 17:
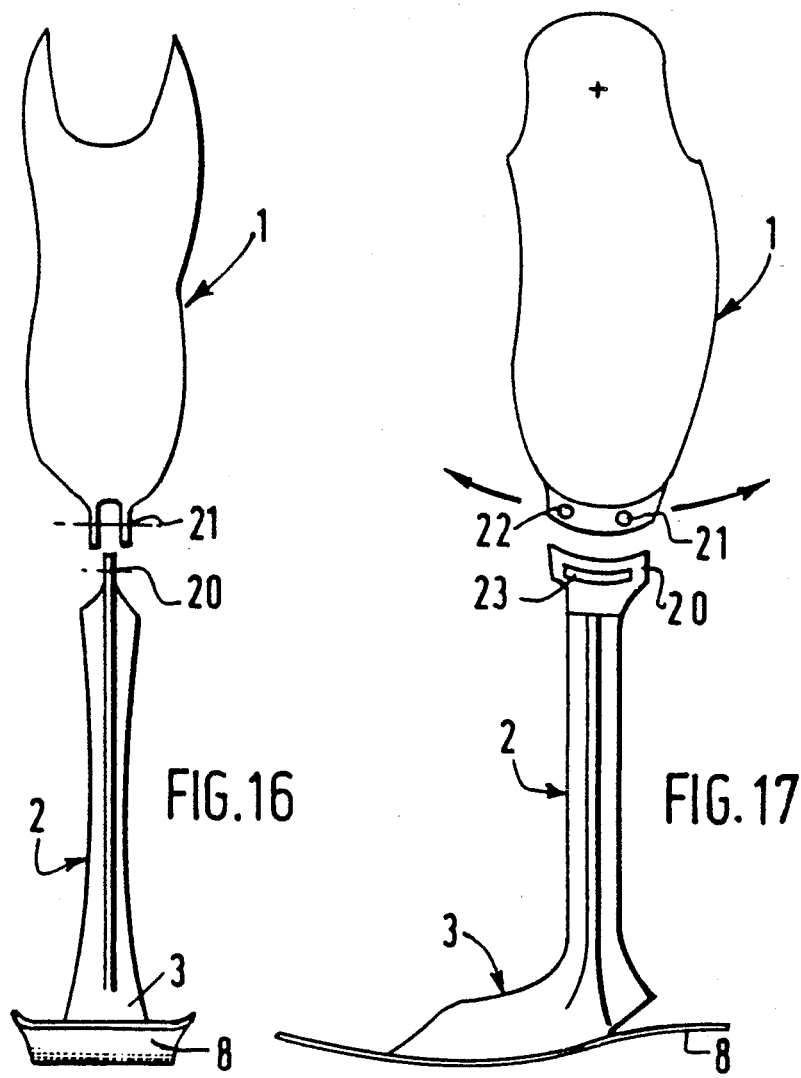
FIGS. 16 and 17 are views, in side elevation and from the rear respectively (sic), of another variant of the prosthesis according to the invention, where the socket is attached to the thermoformed framework.

Finally, FIGS. 16 and 17 illustrate another embodiment of the prosthesis according t the invention. It will be seen in these drawings, in which the elements already described are designated by the same reference numbers, that the socket 1 (sic) is added to the thermoformed monobloc body of the leg part 2 and the prosthetic foot 3.

To this end, a flattened projecting part 20 is provided at the upper end of the leg part 2, while a part 21 of U-shaped cross-section, formed at the base of the socket 1, can fit over this part 20. Holes 22, drilled in the part 21, and an elongate slot 23, formed in the part 20, allow the socket 1 and the leg part 2 to be assembled in a plurality of positions, along a curve whose center and radius correspond to those of the articulation of the knee, for example with the aid of screws and nuts.

The invention thus provides a monobloc prosthesis framework for a leg amputee, which can be manufactured using means known in the art and which nonetheless affords a significant technical advance for the amputee.

I claim:

1. A prosthesis for a leg amputee, comprising a cast framework, covered with a coating material and comprising a socket (1), a leg part (2) and a prosthetic foot (3), one adjoining the other, characterized in that the framework of the leg part (2) and of the prosthetic foot (3) constitutes a monobloc assembly, produced in a single casting operation, and in that the prosthetic foot includes, at the level of a sole of the prosthetic foot, a cut having served for the extraction of a molding core and, at the level of a heel of the prosthetic foot at a rear portion thereof, above the sole, a cut of wedge formation allowing a flexion of the rear of the sole relative to the leg part.

2. A prosthesis according to claim 1, characterized in that the socket (1) is also cast in one piece with the leg part (2) and the prosthetic foot (3) and constitutes with these a monobloc assembly.

3. A prosthesis according to one of claims 1 or 2, characterized in that there is incorporated in the prosthetic foot (3) a sole (8) made of an elastically deformable material.

4. A prosthesis according to claim 3, characterized in that, in the prosthetic foot (3), above the sole (8) made of an elastically deformable material, there is incorporated a metallic spring blade (16), bulged in its center part and bearing at its ends against a front end and a rear end of the sole of the prosthetic foot (3).

5. A prosthesis according to claim 1, characterized in that the leg part (2) includes two lateral ribs (5).

6. A prosthesis according to claim 1, characterized in that the leg part comprises a rear rib (6), formed by a weld resulting from the casting of the framework of the prosthesis.

7. A prosthesis according to claim 1, characterized in that, between the socket and the leg part (2), there are provided, at a rear and at a front, reinforcement ribs (15), in each of which there is embedded a metal wire

(12) stretched obliquely between a base of the socket (1) and the leg part (2).

8. A prosthesis according to claim 1, characterized in that the socket (1) comprises at a lower section thereof, a part (21) of U-shaped cross-section capable of fitting over a projecting part (20) of complementary profile formed at an upper section of the leg part (2), and fixable on the latter with screws and nuts in a plurality of positions.

9. A prosthesis for a leg amputee as claimed in claim 1 wherein the cast framework is thermoformed from a thermoplastic material.

10. A prosthesis for a leg amputee as claimed in claim 1 wherein the cast framework is a laminated substance.

11. A method for producing a prosthesis for a leg amputee according to claim 1 comprising the steps of:
   (a) casting a material into a monobloc framework of a leg part and a prosthetic foot around a suitable core; and then
   (b) cutting the prosthetic foot to extract the core; and then
   (c) forming a cut, at the level of a heel portion of the prosthetic foot and above a sole portion thereof, having a wedge formation allowing for a flexion of a rear of the sole relative to the leg part.

12. A method according to claim 11, characterized in that, prior to the casting, there is fixed under the core (10), used for the casting, a reinforcement sole (8) of an elastically deformable material, in such a way that it is made integral with the monobloc framework during the casting operation, and in that, after this operation, the core (10) is extracted through an opening made in this sole and in the monobloc framework.

13. A method according to claim 12, characterized in that, after the extraction of the core, a spring blade of metal or of another elastically deformable material braced and curved between a front end and a rear end of the prosthetic foot is inserted into the prosthetic foot.

14. A method according to claim 11, in which the socket (1) of the prosthesis is cast at the same time as the monobloc framework of the leg part (2) and of the prosthetic foot (3) of the prosthesis, characterized in that, prior to the casting operation, a head of the core (10) used for the casting is embedded in a plaster cast (11) of a stump of an amputee, in that, after the casting operation, the plaster cast (11) is removed and in that the socket (1) thus cast is cut to the desired shapes.

15. A method for producing a prosthesis for a leg amputee according to claim 11 wherein the casting step is carried out using a thermoplastic material.

16. A method for producing a prosthesis for a leg amputee according to claim 11 wherein the casting step is carried out using a laminated substance.

* * * * *